(12) United States Patent
Balisky

(10) Patent No.: US 7,205,153 B2
(45) Date of Patent: Apr. 17, 2007

(54) ANALYTICAL REAGENT FOR ACID COPPER SULFATE SOLUTIONS

(75) Inventor: Todd Alan Balisky, Corona, CA (US)

(73) Assignee: Applied Materials, Inc., Santa Clara, CA (US)

( * ) Notice: Subject to any disclaimer, the term of this patent is extended or adjusted under 35 U.S.C. 154(b) by 654 days.

(21) Appl. No.: 10/412,484

(22) Filed: Apr. 11, 2003

(65) Prior Publication Data

US 2004/0203165 A1    Oct. 14, 2004

(51) Int. Cl.
G01N 33/20    (2006.01)
G01N 31/16    (2006.01)

(52) U.S. Cl. ............... 436/80; 422/75; 422/79; 422/77; 436/43; 436/50; 436/51; 436/73; 436/150; 436/151; 436/166

(58) Field of Classification Search ......... 422/61, 422/75–77; 436/43, 50–51, 55, 73, 80, 150–151, 436/166

See application file for complete search history.

(56) References Cited

U.S. PATENT DOCUMENTS

| | | | |
|---|---|---|---|
| 3,649,509 A | 3/1972 | Morawetz et al. | 204/238 |
| 3,716,615 A * | 2/1973 | Bauer et al. | 423/35 |
| 3,878,059 A * | 4/1975 | Wechter et al. | 205/781.5 |
| 3,898,042 A * | 8/1975 | Webb et al. | 436/80 |
| 3,920,521 A * | 11/1975 | Michelson et al. | 435/189 |
| 4,045,304 A | 8/1977 | Tezuka | 204/49 |
| 4,110,176 A | 8/1978 | Creutz et al. | 204/52 R |
| 4,176,032 A * | 11/1979 | Stevenson, Jr. | 204/415 |
| 4,276,323 A | 6/1981 | Oka et al. | 427/8 |
| 4,314,823 A | 2/1982 | Rich, Jr. et al. | 23/230 R |
| 4,315,059 A | 2/1982 | Raistrick et al. | 429/112 |
| 4,326,940 A | 4/1982 | Eckles et al. | 204/232 |
| 4,336,114 A | 6/1982 | Mayer et al. | 204/52 R |
| 4,364,263 A | 12/1982 | Sankoorikal et al. | 73/61.1 |
| 4,376,685 A | 3/1983 | Watson | 204/52 R |
| 4,405,416 A | 9/1983 | Raistrick et al. | 204/68 |
| 4,435,266 A | 3/1984 | Johnston | 204/276 |
| 4,468,331 A | 8/1984 | Antle et al. | 210/659 |

(Continued)

FOREIGN PATENT DOCUMENTS

JP    58-182823    10/1983

(Continued)

OTHER PUBLICATIONS

Nakagawa, G. et al, Bulletin of the Chemical Society of Japan 1975, 48, 424-427.*

(Continued)

*Primary Examiner*—Arlen Soderquist
(74) *Attorney, Agent, or Firm*—Patterson & Sheridan, LLP

(57) ABSTRACT

Embodiments of the invention provide an analytical method and analytical reagent solutions for determining the concentration of electrolyte components, such as copper, acid and chloride constituents in an acid or basic metal plating bath using a chemical analyzer. Common methods for measuring the concentration of copper general require two reagent solutions/two steps. This invention provides a novel analytical reagent solution that simplifies the chelating, buffering, and cleaning functions of separate regent solutions required for measuring electrolyte concentration. This has the benefits of reducing chemical inventory and associated dispensing equipment, and thus reducing chemical consumption.

25 Claims, 4 Drawing Sheets

U.S. PATENT DOCUMENTS

| | | | | |
|---|---|---|---|---|
| 4,628,726 A | | 12/1986 | Heikkila et al. | 73/61.1 |
| 4,629,570 A | * | 12/1986 | Kennedy, Jr. | 210/666 |
| 4,631,116 A | | 12/1986 | Ludwig | 204/1 T |
| 4,692,346 A | | 9/1987 | McBride et al. | 427/8 |
| 4,694,682 A | | 9/1987 | Heikkila et al. | 73/61.1 |
| 4,725,339 A | | 2/1988 | Bindra et al. | 204/1 T |
| 4,749,552 A | * | 6/1988 | Sakisako et al. | 422/75 |
| 4,789,445 A | | 12/1988 | Goffman et al. | 204/114 |
| 4,865,992 A | * | 9/1989 | Hach et al. | 436/51 |
| 5,039,381 A | | 8/1991 | Mullarkey | 204/47.5 |
| 5,055,425 A | | 10/1991 | Leibovitz et al. | 437/195 |
| 5,092,975 A | | 3/1992 | Yamamura et al. | 204/198 |
| 5,162,260 A | | 11/1992 | Leibovitz et al. | 437/195 |
| 5,192,403 A | | 3/1993 | Chang et al. | 204/153.1 |
| 5,222,310 A | | 6/1993 | Thompson et al. | 34/202 |
| 5,224,504 A | | 7/1993 | Thompson et al. | 134/155 |
| 5,230,743 A | | 7/1993 | Thompson et al. | 134/32 |
| 5,244,811 A | | 9/1993 | Matthews | 436/146 |
| 5,256,274 A | | 10/1993 | Poris | 205/123 |
| 5,294,554 A | * | 3/1994 | Uchida et al. | 436/73 |
| 5,316,974 A | | 5/1994 | Crank | 437/190 |
| 5,320,724 A | | 6/1994 | Ludwig et al. | 204/153.1 |
| 5,326,165 A | * | 7/1994 | Walthall et al. | 366/165.1 |
| 5,328,589 A | | 7/1994 | Martin | 205/296 |
| 5,368,711 A | | 11/1994 | Poris | 204/193 |
| 5,368,715 A | | 11/1994 | Hurley et al. | 205/82 |
| 5,377,708 A | | 1/1995 | Bergman et al. | 134/105 |
| 5,378,628 A | | 1/1995 | Gratzel et al. | 435/288 |
| 5,429,733 A | | 7/1995 | Ishida | 204/224 R |
| 5,447,615 A | | 9/1995 | Ishida | 204/224 R |
| 5,453,370 A | * | 9/1995 | Triplett et al. | 435/219 |
| 5,516,412 A | | 5/1996 | Andricacos et al. | 204/224 R |
| 5,705,223 A | | 1/1998 | Bunkofske | 427/240 |
| 5,723,028 A | | 3/1998 | Poris | 204/231 |
| 5,908,556 A | | 6/1999 | Cavotta et al. | 210/656 |
| 5,932,791 A | | 8/1999 | Hambitzer et al. | 73/19.01 |
| 6,254,760 B1 | | 7/2001 | Shen et al. | 205/335 |
| 6,391,209 B1 | | 5/2002 | Belongia et al. | 210/748 |
| 6,403,355 B1 | * | 6/2002 | Hagihara et al. | 435/202 |
| 6,471,845 B1 | | 10/2002 | Dukovic et al. | 205/81 |

FOREIGN PATENT DOCUMENTS

| | | |
|---|---|---|
| JP | 63-118093 | 5/1988 |
| JP | 4-131395 | 5/1992 |
| JP | 4-280993 | 10/1992 |
| JP | 6-017291 | 1/1994 |
| WO | 97/12079 | 4/1997 |

OTHER PUBLICATIONS

Schafer, H., Mikrochimica Acta 1978, 2, 321-325.*
Vlasov, Yu. G. et al, Journal of Analytical Chemistry 1982, 37, 1663-1665.*
Hulanicki, A, et al, Analytica Chimica Acta 1984, 158, 343-355.*
Neshkova, M. et al, Mikrochimica Acta 1985, 2, 161-169.*
Konishi, S., Metal Finishing 1965, 63, 58 and 62.*
Ogino, H., Bulletin of the Chemical Society of Japan 1965, 38, 771-777.*
Voydanoff, E. S., Plating 1968, 55, 839-840.*
Seth, R. L., Metal Finishing 1968, 66, 57-58.*
Bauer, D. J. et al, Journal of Metals 1971, 23, 31-33.*
Balana, J., Pinturas y Acabados 1973, 15, 29-34.*
Macca, C., Analytica Chimica Acta 2002, 456, 313-323.*
Colombo, "Wafer Back Surface Film Removal," Central R&D, SGS-Thomson Microelectronics, Agrate, Italy.
Singer, "Wafer Processing," Semiconductor International (Jun. 1998).
Pitney, "NEY Contact Manual," Electrical Contacts for Low Energy Uses (Oct. 1974).

* cited by examiner

ANALYTICAL REAGENT FOR ACID COPPER SULFATE SOLUTIONS

BACKGROUND OF THE INVENTION

1. Field of the Invention

Embodiments of the invention generally relate to a method for measuring the concentration of components in a plating solution useful in electrochemical plating systems.

2. Description of the Related Art

Metallization of sub-quarter micron sized features is a foundational technology for present and future generations of integrated circuit manufacturing processes. More particularly, in devices such as ultra large scale integration-type devices, i.e., devices having integrated circuits with more than a million logic gates, the multilevel interconnects that lie at the heart of these devices are generally formed by filling high aspect ratio, i.e., greater than about 4:1, interconnect features with a conductive material, such as copper. Conventionally, deposition techniques such as chemical vapor deposition (CVD) and physical vapor deposition (PVD) have been used to fill these interconnect features. However, as the interconnect sizes decrease and aspect ratios increase, void-free interconnect feature fill via conventional metallization techniques becomes increasingly difficult. Therefore, plating techniques, i.e., electrochemical plating (ECP) and electroless plating, have emerged as promising processes for void free filling of sub-quarter micron sized high aspect ratio interconnect features in integrated circuit manufacturing processes.

In an ECP process, for example, sub-quarter micron sized high aspect ratio features formed into the surface of a substrate (or a layer deposited thereon) may be efficiently filled with a conductive material, such as copper. ECP plating processes are generally two stage processes, wherein a seed layer is first formed over the surface features of the substrate (generally through PVD, CVD, atomic layer deposition (ALD), or other deposition process in a separate tool), and then the surface features of the substrate are exposed to an electrolyte solution (in the ECP tool), while an electrical bias is applied between the seed layer and a copper anode positioned within the electrolyte solution. The electrolyte solution is generally rich in copper ions ($Cu^{2+}$) that are to be plated onto the surface of the substrate, and therefore, the application of the electrical bias, i.e., configuring the substrate as the cathode, causes these ions to be plated onto the seed layer, thus depositing a layer of the ions on the substrate surface that may fill the features.

Generally, ECP electrolytes have both inorganic and organic compounds/components at low concentrations. Typical inorganics include copper sulfate ($CuSO_4$), sulfuric acid ($H_2SO_4$), and trace amounts of chloride ($Cl^-$) ions. Other components include accelerators, suppressors, and levelers. An accelerator is sometimes called a brightener or anti-suppressor. A suppressor may be a surfactant or wetting agent, and is sometimes called a carrier. A leveler is also called a grain refiner or an over-plate inhibitor. The sulfuric acid generally operates to adjust the acidity/pH and conductivity of the solution, while the copper chloride provides negative chlorine ions needed for proper action of suppressor molecules and facilitates proper anode dissolution.

Although simple in principle, copper plating relies in practice on the use of proper components in the electrolyte to determine the properties of the copper being deposited. Because of depletion, analysis of the processing components is required periodically during the plating process. If the concentrations change, or if the components get out of balance, the quality of the plated copper deteriorates. In addition, the depletion of certain components is not generally constant over time, nor is it generally possible to correlate the plating solution composition with the duration of the plating solution use. Thus, the component concentrations may eventually exceed or fall below a tolerance range for optimal and controllable plating. It is very important for ECP systems to monitor and control concentrations of inorganic and organic components, especially as the technological demands on the copper become more stringent.

Chemical analyzers implementing different analytical principles such as end-point titration and back titration, and others, are used to analyze the concentrations of components, such as dissolved copper ions, in metal plating baths. The chemical analyzer is typically coupled to a metal plating apparatus, such as an electrochemical plating (ECP) apparatus for depositing metal films on semiconductor devices. Similarly, these analytical principles can be applied to manually analyze component concentrations.

"Titration" for measurement of copper concentration is accomplished through adding a quantity of a known concentration of reactants that reacts with the copper. The progress of the reaction is measured by the amount of reaction product produced by the chemical reaction between copper and the reactants, and an end point can be detected and correlated to a copper concentration in the electrolyte. The titration method generally requires two or more reagent solutions in two or more steps, for example, at least one chelating agent solution to titrate the metal ions, such as copper, aluminum, and others, and at least another pH-buffering agent solution, such as an ammonium hydroxide solution, to keep the pH in an effective range for metal chelating reaction to occur. If this is not done, then most chelating agents combine or react with the metal ions, such as copper, impractically slowly such that the complete reaction time for each reaction adds up to a impractically long analysis time.

Another method that may be used is a "back titration" method, which employs an excess amount of a chelating agent solution for a first chelating reaction to occur in one waiting period rather than multiple waiting periods for the reaction to complete, and another titrating reagent solution to react with the excess amounts of the chelating agent in the first chelating agent solution or with the amount of by-products (e.g. acids, bases, aggregates, precipitates) formed after the first chelating reaction. Again, two or more reagent solutions are needed. Such titrating reagent may react faster with the chelating agent than the metal ions to be measured. Suitable titrating reagent solution includes a solution having metal ions, such as zinc ions, to titrate the excess chelating agent, and other buffers, such as a hydroxide solution (e.g. sodium hydroxide, etc.), to titrate the pH back to the original pH. Another example is to use an excess amount of a potassium iodide solution to reduce or convert copper ions from $Cu^{+2}$ to $Cu^{+1}$, thus creating an amount of iodine equal to the initial copper II ions ($Cu^{+2}$) present. Since this reaction is relatively slow and not reliably measured, a titrating reagent solution such as a sodium thiosulfate solution is then used to oxidize the iodine back to iodide ion, a reaction that can be repeatably detected. For back titration, the concentration of the unknown electrolyte component can be measured by considering the excess amount of the chelating agent in the first chelating solution and the required amount of titrating reagent in the titrating reagent solution. One problem is that the reaction by-products, such as precipitates, released acids, or others, may cause build up in the chemical analyzer or interfere with any of the ongoing chemical reactions. In addition, titration and back titration methods have the limitations in that they use more chemicals, are time consuming for different reactions to occur, are subject to fluctuation of the pH of different solutions that may not be optimal for the different reactions to occur, and have a lack of a sharp or definable reaction end point.

Therefore, a need exists to provide methods and reagents for real-time analysis of electrolyte components in a processing system, either manually or through the integration of one or more chemical analyzers.

SUMMARY OF THE INVENTION

Embodiments of the invention provide an analytical method and formulations for determining the concentration of a component in a plating bath manually or using a chemical analyzer. The method includes providing an analytical reagent solution, sampling a testing solution from the plating bath, measuring a series of chemical responses of the testing solution reacting with two or more doses of the analytical reagent solution, and calculating the concentration of the component in the plating bath from the measurements of the series of chemical responses. The analytical reagent solution for determining the component concentration includes at least one chelating agent, at least one pH buffering agent, and, optionally, at least one cleaning agent.

In one embodiment, an analytical method for determining the concentration of a component in a plating bath includes providing an analytical reagent solution having at least one chelating agent selected from the group consisting of ethelenediaminetetraacetic acid ($H_4EDTA$), ethelenediaminetetraacetic acid salts, ethelenediaminetetraacetic acid disodium salt ($Na_2H_2EDTA$), tetrasodium ethelenediaminetetraacetic acid ($Na_4EDTA$), magnesium disodium ethelenediaminetetraacetic acid ($MgNa_2EDTA$), cyclohexanediaminetetraacetic acid (CDTA), N-2-hydroxyethyl-ethylenediamine-N,N,N'-triacetic acid tri sodium salt (HEDTA), triethylene tetramine hexaacetic acid (TTHA), nitrilotriacetic acid (NTA), derivatives, hydrates, anhydrates, metal salts, and combinations thereof, at least one pH buffering agent selected from the group consisting of ammonia, ammonia chloride, a hydroxide salts such as sodium hydroxide, ammonium hydroxide, magnesium hydroxide, and calcium hydroxide, their derivatives, and combinations thereof in an amount sufficient to adjust the pH of the analytical reagent solution to a range of from about 7 to about 10, and water. The method further includes providing a testing solution having a portion of the plating bath therein, measuring a series of chemical responses of the testing solution reacting with two or more doses of the analytical reagent solution, and calculating the concentration of the component in the plating bath from the measurements of the series of chemical responses.

In another embodiment, an analytical method for determining the concentration of a component in a plating bath includes combining two or more reagent solutions for at least one chelating and at least one buffering into one analytical reagent solution, wherein the analytical reagent solution includes at least one chelating agent selected from the group consisting of ethelenediaminetetraacetic acid ($H_4EDTA$), ethelenediaminetetraacetic acid salts, ethelenediaminetetraacetic acid disodium salt ($Na_2H_2EDTA$), tetrasodium ethelenediaminetetraacetic acid ($Na_4EDTA$), magnesium disodium ethelenediaminetetraacetic acid ($MgNa_2EDTA$), cyclohexanediaminetetraacetic acid (CDTA), N-2-hydroxyethyl-ethylenediamine-N,N,N'-triacetic acid tri sodium salt (HEDTA), triethylene tetramine hexaacetic acid (TTHA), nitrilotriacetic acid (NTA), derivatives, hydrates, anhydrates, metal salts, and combinations thereof, a pH buffering agent selected from the group consisting of ammonia, ammonia chloride, a hydroxide salts such as sodium hydroxide, ammonium hydroxide, magnesium hydroxide, and calcium hydroxide, their derivatives, and combinations thereof in an amount sufficient to adjust the pH of the analytical reagent solution to a range of from about 7 to about 10, and water. The method further includes performing an analytical technique for a portion of the plating bath using the analytical reagent solution to determine the concentration of the component.

In another embodiment, an analytical method for determining the concentration of a component in a plating bath includes providing a testing solution having a portion of a plating bath therein, adding a pre-dose volume of an analytical reagent solution to react with the testing solution, and adding one or more doses of a second volume of the analytical reagent solution to react with the testing solution. The method further include measuring a series of chemical responses of the testing solution reacting with the analytical reagent solution, obtaining an endpoint dose, and calculating the concentration of the component in the plating bath from the measurements of the series of chemical responses and the endpoint dose.

In another embodiment, an analytical reagent solution for determining the concentration of a component in a plating bath is provided. The analytical reagent solution includes at least one chelating agent selected from the group consisting of ethelenediaminetetraacetic acid ($H_4EDTA$), ethelenediaminetetraacetic acid salts, ethelenediaminetetraacetic acid disodium salt ($Na_2H_2EDTA$), tetrasodium ethelenediaminetetraacetic acid ($Na_4EDTA$), magnesium disodium ethelenediaminetetraacetic acid ($MgNa_2EDTA$), cyclohexanediaminetetraacetic acid (CDTA), N-2-hydroxyethyl-ethylenediamine-N,N,N'-triacetic acid tri sodium salt (HEDTA), triethylene tetramine hexaacetic acid (TTHA), nitrilotriacetic acid (NTA), derivatives, hydrates, anhydrates, metal salts, and combinations thereof, and at least one pH buffering agent selected from the group consisting of ammonia, ammonia chloride, a hydroxide salt solution, which may be sodium hydroxide, ammonium hydroxide, magnesium hydroxide, and calcium hydroxide, their derivatives, and combinations thereof, in an amount sufficient to adjust the pH of the analytical reagent solution to a range of from about 7 to about 10. Optionally, the analytical reagent solution further includes at least one cleaning agent.

BRIEF DESCRIPTION OF THE DRAWINGS

So that the manner in which the features of the invention are attained and can be understood in detail, a more particular description of the invention, briefly summarized above, may be had by reference to the embodiments thereof, which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The words and phrases used herein should be given their ordinary and customary meaning by one skilled in the art unless otherwise further defined.

Embodiments of the invention include an analytical method and formulations for determining the concentration of an electrolyte constituent of interest in an acidic or basic electrochemical plating bath containing multiple components. The method is performed to analyze electrolyte constituents independently, regardless of the interference from other components, and is performed by extracting a sample of electrolyte (e.g. a testing solution) from a test port followed by transferring the sample to a remote chemical analyzer or performing analysis manually. The electrolyte composition is then adjusted according to the results of the analyses. This analysis may be conducted on a frequent bases, so that the concentration in the electrolyte can be controlled and maintained in a narrow range if desired.

Figure 1:
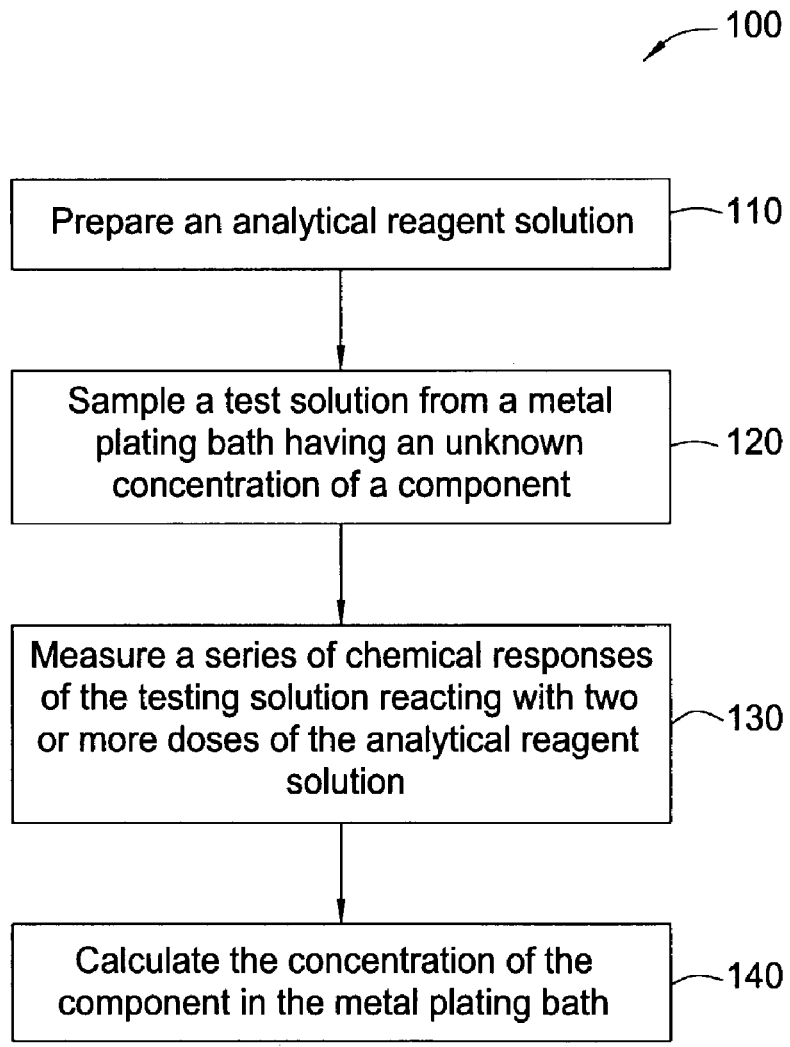
FIG. 1 is a flow diagram illustrating an exemplary analytical method.

FIG. 1 is a flow chart illustrating an exemplary analytical method 100 of the invention to analyze the concentration of one or more components in plating baths containing multiple components. The method 100 of FIG. 1 includes preparing an analytical reagent solution at step 110, and sampling a testing solution from a plating bath, such as a plating bath for various metals, having an unknown concentration of a component at step 120. At step 130, a series of chemical responses of the testing solution reacting with two or more doses of the analytical reagent solution is measured, and the concentration of the component in the plating bath is calculated from the measurements of the series of chemical responses at step 140.

In one embodiment of the invention, the concentration of a component in a plating bath of unknown concentration can be determined by including the analytical reagent solution described herein into an analytical technique, such as titration and others, and measuring a series of chemical responses to find a titration endpoint or an endpoint dose, either manually or using an automated chemical analyzer. Manual analyses include, but are not limited to, the use of colorimetric indicators and others, such as the addition of appropriate amounts of indicator dyes or dye strips. For example, bromothymol blue, bromophenol blue, and others can be used as indicator dyes. Applicable chemical analyzers include, but are not limited to, those methods employing titration methods with potentiometric endpoint detection. The chemical analyzers typically have a sensor or an electrode made of various types of metals (e.g. a platinum electrode), to measure a chemical response. For example, an automated titration system, available from Fisher Scientific International, Inc., and a G2 auto-titrator made by Parker Technology, can be used herein to measure changes of electro potential (e.g. change in voltage). In addition, the method 100 can be employed to various analytical principles, such as "titration" or "back titration", for analyzing component concentration.

At step 110, an analytical reagent solution for determining an unknown concentration of a component in a plating bath is provided. The analytical reagent solution for determining the concentration of the component, such as copper, chloride, or other metals, generally includes a chelating agent and a pH buffering agent to neutralize the acidity of the chelating agent. The analytical reagent solution is prepared and pre-mixed into one analytical reagent solution before applying an analytical technique, such as titration and back titration, to analyze the concentration of the plating component in a testing solution. It was found that by combining the chelating agent and the pH buffering agent together into one analytical reagent solution, a precise endpoint concentration or endpoint dose during titration analyses and/or a stronger chemical signal from chemical analyzers can be obtained. This result may generally come from the fact that a single analytical reagent solution is neither over buffered or under buffered, rather, the pH buffering agent is added to balance the acidity generated from the chelating reaction because it is pre-mixed with the chelating agent into a desired proportion.

At step 120, a testing solution is sampled from an electrolyte for plating having the component to be analyzed. In some cases, the testing solution is prepared by dilution of a sample of electrolyte/plating bath from an electrochemical plating (ECP) system into a small aliquot, such as a working concentration range for manual or automated analyses.

At step 130, two or more doses of the analytical reagent solution are added successively into and react with the sampled testing solution in order to obtain a series of chemical response measurements. Small doses of the analytical reagent solution are added until a titration endpoint of the chemical response measurement or an endpoint dose is reached, for example, as indicated by a color change (manual analysis) or a peak/spike in the potentiometric reading per dose (automated analysis). A dose in microliter range, such as about 2 to about 5 microliters, is generally used depending on the sensitivity of the chemical response measurement used. At step 140, the concentration of the component in the plating bath is calculated from the measurements of the series of chemical responses.

In another embodiment of the invention, a method for determining the concentration of an component, when performing the method 100 of FIG. 1, includes adding a pre-dose volume of an analytical reagent solution to react with the testing solution and allow a chelating reaction to occur very fast (e.g. in about 3 or more seconds), and then adding one or more doses of a second volume of the analytical reagent solution subsequently. The subsequent one or more doses are added for the chelating reaction to occur slowly in order to obtain a precise endpoint concentration, such as a stronger chemical signal from the chemical analyzer, for the electrolyte component to be analyzed. In general, the pre-dose volume of the analytical reagent solution is lager than the second subsequent one or more doses. For example, the pre-dose volume of the analytical reagent solution can be about 10 to about 100 times of the volume of the second subsequent one or more doses. The pre-dose volume of the analytical reagent solution is generally larger than the second volume. For example, the pre-dose volume can include up to half of the estimated final volume of the analytical reagent solution required to reach a titration endpoint. As a result, the overall analysis time can be shortened.

In general, the analytical reagent solution includes a chelating agent and a pH buffering agent. Optionally, the analytical reagent solution further includes a cleaning agent. The cleaning agent can be selected from a variety of compounds that, when prepared in solution, help to dissolve any by-products, build-ups, insoluble parts formed in any of the solutions or analytical equipments used or during other types of component analyses that use the same equipments (e.g. silver chloride is formed when analyzing chloride concentration of a plating bath using silver nitrate). In addition, the cleaning agent is preferably selected from non-volatile compounds, however, volatile compounds may be used.

The compounds suitable as the cleaning agent for the analytical reagent solution include, but are not limited to, ammonia, ammonia salts, amine(—NH2) -containing, thiol (—SH)-containing, thio(—SC)-containing, and thionate (—SO)-containing compounds, their derivatives, and combinations thereof. For example, amino acids include both an amine (—NH$_2$) and carboxylic acid (—COOH) groups. One example is glycine (Gly) and another example that may be used herein is glutamine (Gln). These compounds generally provide cleaning function (e.g. dissolves silver chloride during chloride analyses), are readily dissolves in water, non-toxic, low cost, chemically stable, physically stable (i.e. do not precipitate, gel, or otherwise change their physical forms over time), and do not affect the copper analysis in the chelating reaction with the chelating agent of the analytical solution. In general, these were found to be molecules that contained both an amine (NH$_2$) and carboxylic acid (COOH) groups.

These compounds can be made into the analytical reagent solution to a final concentration of from about 0.1 g/L to about 200 g/L depending on the compounds used. The relative concentration of the cleaning agent, such as a solution made from amine-containing compounds, is not critical. It may be raised to increase cleaning efficiency or lowered to decrease cost per unit volume. One working example of the cleaning agent that can be used is at a final concentration of about 25 g/L of glycine in the analytical reagent solution because of its lower cost and physical stability. Another example is at a final concentration of about 100 g/L of glycine.

In another embodiment, a method for determining the concentration of an component in an unknown plating bath, when performing the method 100 of FIG. 1, includes combining the reagents for chelating, buffering, and, optionally, cleaning into one analytical reagent solution in order to reduce chemical consumption, chemical waste thus produced, and associated metering and dispensing equipments. Thus, the analytical reagent solution prepared at step 110, does not generate or release acid while chelating metal ions, such as copper ions. Since the pH buffering agent provides is a base and provides hydroxide ions to combine in correct proportion to the concentration of the chelating agent, there is no need to add an excess of chelating agent prior to the start of the analysis. Besides, since the method does not require a separate source for a titrating agent or a pH buffering agent to back titrate the chelating agent, a wider analytical range can be obtained. One single analytical reagent solution is prepared and kept at a constant pH value.

Many chelating agents may be used herein for making the analytical solution. One common chelating agent is, disodium ethelenediaminetetraacetic acid (Na$_2$H$_2$EDTA, disodium EDTA, ethylenedinitrilo tetraacetic acid disodium salt). Others include, but are not limited to, ethelenediaminetetraacetic acid salts, cyclohexanediaminetetraacetic acid (CDTA, 1,2-cyclohexylenedinitrilotetraacetic acid, CDTE, C$_y$DTA), N-2-hydroxyethyl-ethylenediamine-N,N,N'-triacetic acid tri sodium salt (HEDTA), triethylene tetramine hexaacetic acid (TTHA), nitrilotriacetic acid (NTA, tricarboxymethyl amine, triglycine). Other forms, derivatives, hydrates, anhydrates, metal salts, or combinations of the chelating agent described herein can also be used, so long as the concentration of the pH buffering agent is adjusted accordingly. For example, different salt content of ethelenediaminetetraacetic acid (EDTA, ethylenedinitrilo tetraacetic acid), such as ethelenediaminetetraacetic acid (H$_4$EDTA) or tetrasodium ethelenediaminetetraacetic acid (Na$_4$EDTA) can also be used. However, these reagents are usually more expensive and/or is less purified than the more commonly available disodium ethelenediaminetetraacetic acid variety. Another example of different metal salts of EDTA that can be used herein is magnesium disodium ethelenediaminetetraacetic acid (MgNa$_2$EDTA), which exhibits a very strong endpoint signal after titration when included into the analytical solution.

The effective pH range may depend on the chelating agent used. For example, an effective pH range for ethelenediaminetetraacetic acid (EDTA), to react with copper is at a pH of about 7 to about 10, such as a pH of about 8 to about 9. In addition, the binding strength of the chelating agent is pH dependent. For example, when EDTA actually reacts with copper ions, its binding strength is inhibited at lower pH. Thus, the pH is generally calculated to provide adequate binding strength and facilitate reaction.

Suitable pH buffering agents include, but are not limited to, ammonia chloride, any of hydroxide salts, such as sodium hydroxide, ammonium hydroxide, magnesium hydroxide, and calcium hydroxide, their derivatives, and combinations thereof. In one embodiment, the pH buffering agent is a non-volatile solution. In some cases, the pH buffering agent is provided not only to adjust the pH of the chelating agent, but also to clean any of the solutions or equipments used during component analyses.

In general, the chelating agent in the analytical reagent solution can be adjusted to a final concentration of from about 0.01M to about 0.8M, such as from about 0.1M to about 0.5M, depending on the concentration of the pH buffering agent used to balance the acidity of the chelating agent and to increase the solubility of the chelating agent.

The pH buffering agent in the analytical reagent solution can be adjusted, to a final concentration of between about 0.01M and about 0.8M, such as between about 0.1M and about 0.5M, depending on the concentration of the chelating agent. The relative concentration of the pH buffering agent is not critical, so long as its molarity is between about one to about two times the molarity of the chelating agent, for example, a ratio of about 1.5:1 in molarity can be used. Solutions of the pH buffering agent at or above two times the molarity of the chelating agent can have a different, and in some cases non-stoichiometric titration curve. Another benefit of combining the chelating agent and the pH buffering agent is that the pH buffering agent increases the solubility of the chelating agent. This allows formulating a more concentrated, and in turn more economical, analytical solution.

For example, the analytical reagent solution for determining copper concentration generally includes a mixture of ethelenediaminetetraacetic acid, and sodium hydroxide. One formulation is the addition of about 0.2M of ethelenediaminetetraacetic acid to about 0.3M of sodium hydroxide to a pH of about 8 to about 10. The analytical reagent solution can further include L-glycine. One formulation is about 0.1M of disodium ethelenediaminetetraacetic acid (Na$_2$EDTA), about 25 g/L of L-glycine, and about 0.15M of sodium hydroxide adjusted to a pH of about 8 to about 10. Another formulation is about 0.4M of disodium ethelenediaminetetraacetic acid (Na$_2$EDTA), about 100 g/L of L-glycine, and about 0.6M of sodium hydroxide (NaOH) adjusted to a pH of a pH of about 8 to about 9. They are equally effective in analyzing copper concentration but the analytical reagent solution prepared at higher concentration may be used to reduce chemical consumption.

Another example of the analytical reagent solution includes a mixture of disodium ethelenediaminetetraacetic acid, and magnesium hydroxide to form a solution of magnesium disodium ethelenediaminetetraacetic acid ($MgNa_2EDTA$). One formulation is the addition of about 0.2M of disodium ethelenediaminetetraacetic acid to about 0.3M of magnesium hydroxide to a pH of about 8 to about 10. Another formulation for the analytical reagent solution is about 0.4M of magnesium disodium ethelenediaminetetraacetic acid ($MgNa_2EDTA$) and about 100 g/L of glycine at a pH of about 8 to about 10, where a stronger endpoint signal is needed. The use of magnesium disodium ethelenediaminetetraacetic acid into the analytical reagent solution has the advantages of being simpler to manufacture than a 3 component formulation and having the remaining protons already displaced from the ethelenediaminetetraacetic acid (EDTA) by the magnesium cation and therefore not requiring neutralization by a hydroxide-containing compound.

Electrochemical Plating (ECP) System:

Embodiments of the invention provide analytical methods that can be performed in various electrochemical plating systems. An electrochemical plating system generally includes a mainframe having a mainframe substrate transfer robot, a loading station disposed in connection with the mainframe, one or more processing cells disposed in connection with the mainframe, and an electrolyte supply fluidly connected to the one or more electrical processing cells. Generally, the electrochemical plating system includes a system controller for controlling an electrochemical plating process and related components, a spin-rinse-dry (SRD) station disposed between the loading station and the mainframe, and an electrolyte replenishing system including an integrated chemical analyzer.

One example of an electrochemical plating system that may be used herein is an Electra integrated Electro-Chemical Plating (iECP) System available from Applied Materials, Inc., of Santa Clara, Calif. In addition, any system enabling electrochemical processing using the analytical methods or techniques described herein may also be used.

Figure 2:
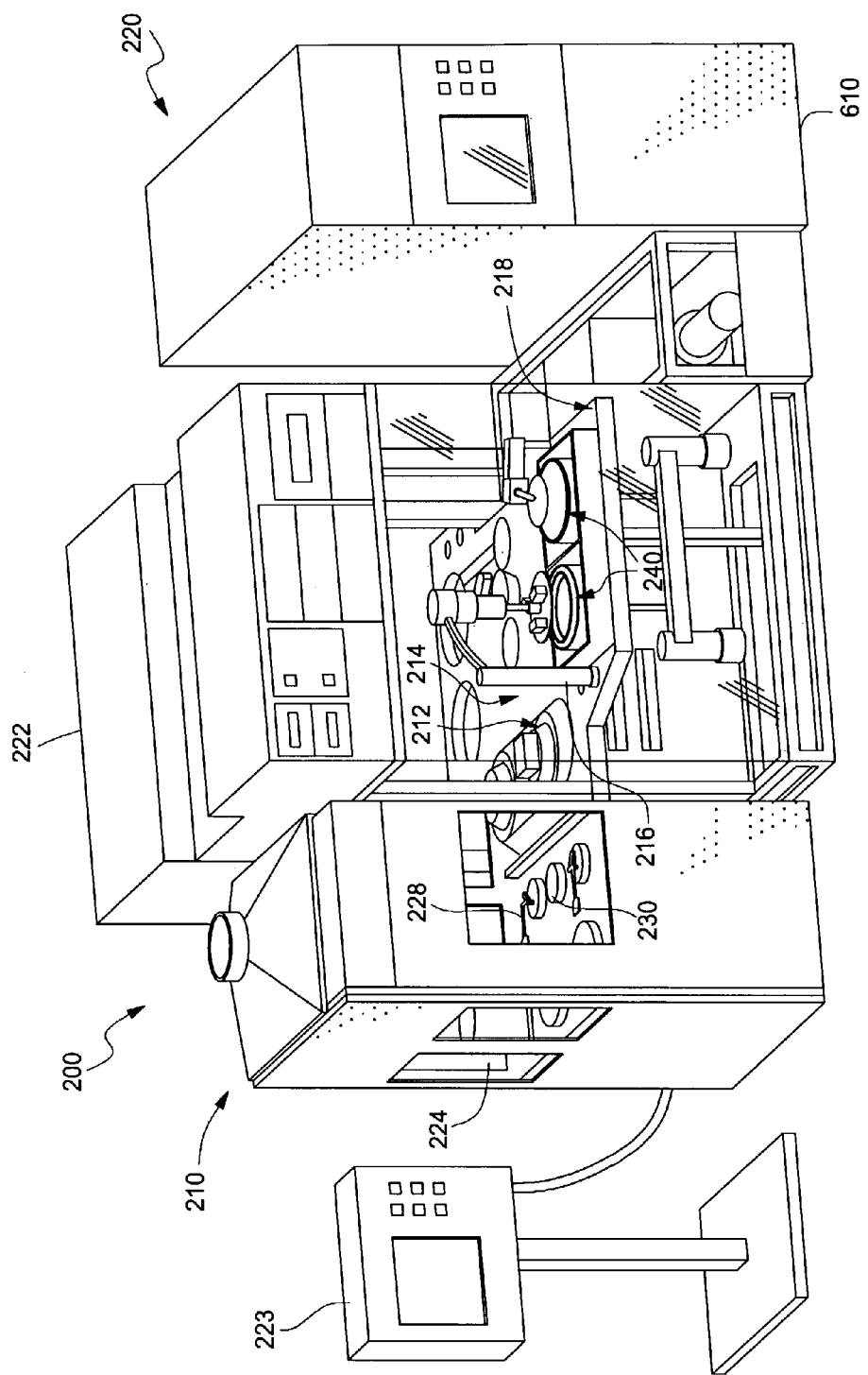
FIG. 2 is a perspective view of an electroplating system platform useful to perform methods described herein.

FIG. 2 is a perspective view of an electroplating system platform 200 of the invention. The electroplating system platform 200 generally includes a loading station 210, a spin-rinse-dry (SRD) station 212, a mainframe 214, and an electrolyte replenishing system 220. Additionally, the electroplating system platform 200 is enclosed in a clean environment using panels, such as plexiglass panels.

The mainframe 214 generally includes a mainframe transfer station 216 and a plurality of processing stations 218. Each processing station 218 includes one or more processing cells 240. An electrolyte replenishing system 220 is positioned adjacent the electroplating system platform 200 and connected to the process cells 240 individually to circulate electrolyte used for the electroplating process. The electroplating system platform 200 also includes a control system 222, typically a programmable microprocessor. The control system 222 also provides electrical power to the components of the system and includes a control panel 223 that allows an operator to monitor and operate the electroplating system platform 200.

The loading station 210 typically includes one or more substrate cassette receiving areas 224, one or more loading station transfer robots 228 and at least one substrate orientor 230. The number of substrate cassette receiving areas, loading station transfer robots 228, and substrate orientor 230 included in the loading station 210 can be configured according to the desired throughput of the system. A substrate cassette containing substrates is loaded onto the substrate cassette receiving area 224 to introduce substrates into the electroplating system platform. The loading station transfer robot 228 transfers substrates between the substrate cassette and the substrate orientor 230. The substrate orientor 230 positions each substrate in a desired orientation to ensure that each substrate is properly processed. The loading station transfer robot 228 also transfers substrates between the loading station 210 and the SRD station 212.

Figure 3:
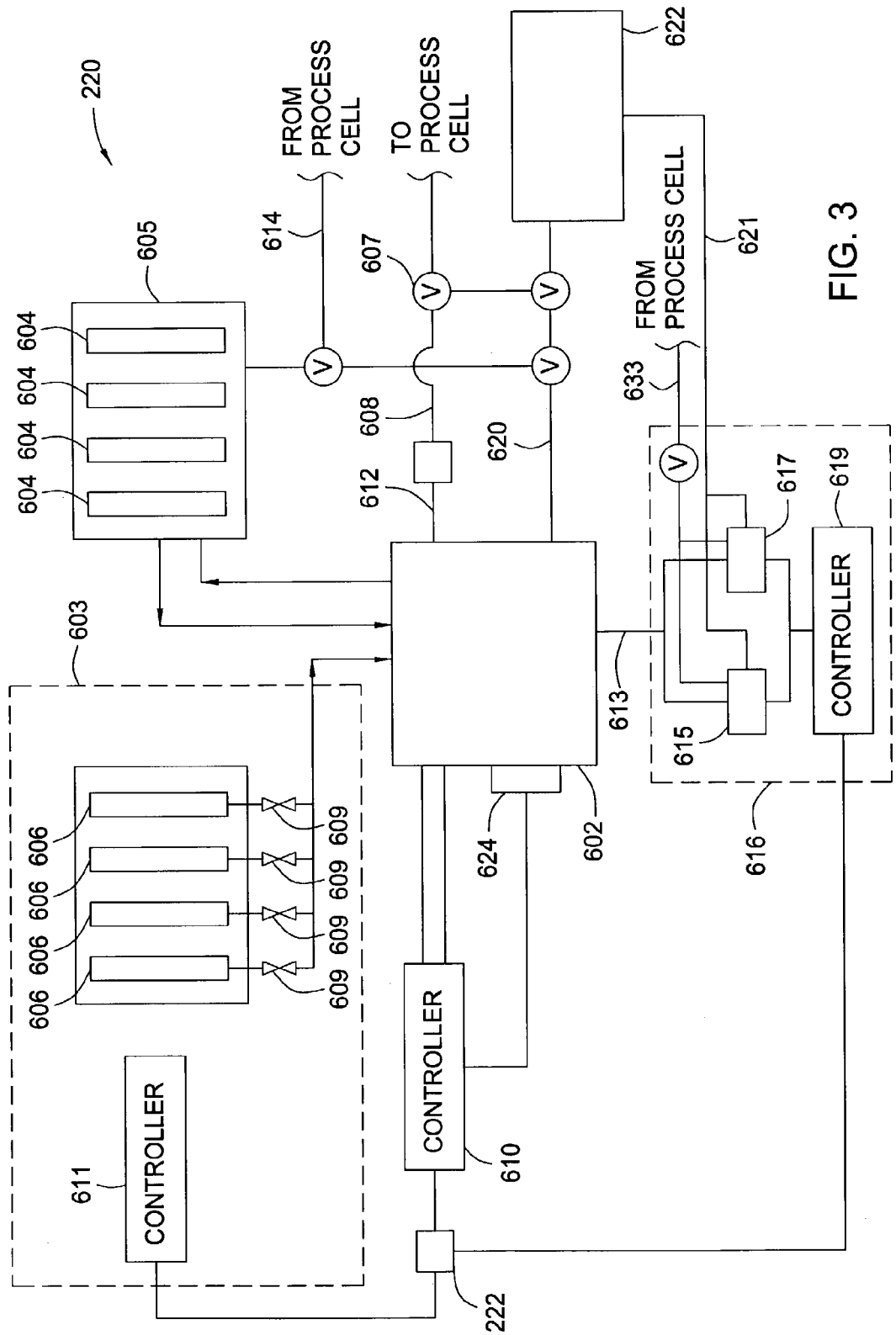
FIG. 3 is a schematic diagram of one embodiment of an electrolyte replenishing system.

FIG. 3 is a flow chart illustrating the electrolyte replenishing system 220, which includes a main controller 610, a main electrolyte tank 602, a dosing module 603, a filtration module 605, a chemical analyzer module 616, and an electrolyte waste disposal system 622 connected to the analyzing module 616 by an electrolyte waste drain 620. The electrolyte replenishing system 220 provides the electrolyte to the electroplating process cells 240 for the electroplating process. One or more controllers, such as controller 610, 611, and 619, control the composition of the electrolytes in the main tank 602 and the operation of the electrolyte replenishing system 220.

The controllers 610, 611, and 619 are usually independently operable but are typically integrated with the control system 222 of the electroplating system platform 200 to provide real-time analyses of the electroplating process and control of the chemical analyzer module 616, the dosing module 603, and other components. Alternatively, the chemical analyzer module 616 and the dosing module 603 may be integrated into one single module and may be controlled by one or more controllers to monitor and replenish the electrolyte from the electroplating process cells 240.

The main electrolyte tank 602 provides a reservoir for electrolyte and is connected to each of the electroplating process cells 240 through one or more fluid pumps 608, an electrolyte supply line 612, and valves 607. A heat exchanger 624 or a heater/chiller, which is disposed in thermal connection with the main tank 602 and operated by the controller 610, controls the temperature of the electrolyte stored in the main tank 602.

The dosing module 603 is connected to the main tank 602 by a supply line and includes a plurality of source tanks 606, or feed bottles, a plurality of valves 609, and a controller 611. The source tanks 606 contain the inorganic chemicals needed for composing the electrolyte and typically include deionized water, copper sulfate ($CuSO_4$), sulfuric acid ($H_2SO_4$), hydrochloric acid (HCl), and other components. The valves 609 associated with each source tank 606 regulate the flow of inorganic chemicals to the main tank 602. Activation of the valves 609 is accomplished by the controller 611, which is preferably connected to the control system 222 to receive signals therefrom.

The electrolyte filtration module 605 includes a plurality of filter tanks 604. An electrolyte return line 614 is connected between each of the process cells 240 and one or more filter tanks 604. The filter tanks 604 continuously remove the undesired solids in the used electrolyte before returning the electrolyte to the main tank 602 for re-use and replenishing, and facilitate re-circulation and filtration of the electrolyte in the main tank 602 to help maintain a consistent level of purity and thorough mixing of the electrolyte in the main tank 602.

The chemical analyzer module 616 includes at least one, and typically two or more, analyzers 615, 617 operated by the controller 619 and integrated with the control system 222 of the electrochemical plating system 200. The analyzer module 616 is fluidly coupled to the main tank 602 by a sample line 613 to provide continuous flow of electrolyte, standard plating solutions, supporting electrolyte solution, etc. from the main electrolyte tank 602 to the chemical analyzers, such as analyzers 615, 617. The analyzer module 616 is also coupled to the waste disposal system 622 by an outlet line 621.

The analyzer module 616 is also coupled to the one or more process cells 240 by an inlet line 633 to provide real-time chemical analysis of the chemical composition of the electrolyte inside each process cell 240 by the chemical analyzers, such as analyzers 615, 617. The number of analyzers required for a particular processing tool depends on the composition of the electrolyte. A first analyzer may be an inorganic analyzer, for example, an auto-titration analyzer to determine the concentrations of inorganic substances in the electrolyte, and the second analyzer may be an organic analyzer, for example, a cyclic voltammetric stripper (CVS), to determine the concentrations of organic substances. After the concentrations of specific chemical components of the electrolyte are analyzed, the dosing module 603 is then activated to deliver the proper proportions of the chemicals to the main tank in response to the information obtained by the chemical analyzer module 616.

Most analyzers are commercially available from various suppliers. A suitable auto-titration analyzer is available from Applied Materials, Inc. of Santa Clara, Calif., such as the G2 titration analyzer™, and a cyclic voltammetric stripper is available from ECI Technology, Inc. of East Rutherford, N.J., such as the Quali-line™ QLCA analyzer. The auto-titration analyzer determines the concentrations of inorganic substances such as copper, chloride, and acid. The cyclic voltametric stripper determines the concentrations of organic substances such as various components used as electrolytes in a plating bath.

The analyzers 615, 617 typically include standards and calibration schemes that enable the controller 619 to compensate for the drifts in measurements as the electrodes or sensors in the analyzers 615, 617 become corroded due to repeated use. The standards and calibration schemes are grouped according to the substances being analyzed by the analyzer.

For example, an auto-titration analyzer includes standards and calibration schemes for the inorganic substances, and a CVS analyzer includes standards and calibration schemes for the organic substances. For example, Table 1 provides three standards for an analysis of copper and chloride contents in a plating bath at a process window between the low and high standards. By interpolating the relationship between the known contents in the standards and the measurements of an analyzer, and using various analytical techniques, the analyzer becomes calibrated to provide accurate analysis of the substances in a testing plating bath.

TABLE 1

Standards for copper and chloride contents

|  | Copper | Chloride |
|---|---|---|
| Standard 1 (low) | 40 g/l | 40 ppm |
| Standard 2 (medium) | 50 g/l | 70 ppm |
| Standard 3 (high) | 60 g/l | 100 ppm |

In one embodiment of the invention, the method 100 of FIG. 1 as provided herein is integrated with the controller 619 for the chemical analyzer module 616 and the control system 222 for the electrochemical plating system 200.

In operation, a sample of supporting-electrolyte solution prepared according to embodiments of the invention, such as the step 110 of FIG. 1, is flowed to the analyzer module 616 from the main electrolyte tank 602 via the sample line 613. A portion of the sample is delivered to the auto-titration analyzer 615 and a portion is delivered to the CVS 617 for the appropriate analysis. The controller 619 initiates command signals to operate the analyzers 615 and 617 in order to generate data and electrochemical responses of the supporting-electrolyte solution are measured by the analyzers 615, 617. The controller 619 also initiates the next step, such as the step 120 of FIG. 1, for the flowing of an unknown sample of electrolyte or a portion of the unknown testing sample from the process cell 240 to the analyzer module 616 via the inlet line 633.

To analyze component concentrations in electroplating solutions, plating responses are measured for various solutions, the analytical solution, testing solutions, standard solutions, calibration solutions, and/or in the presence or absence of components, depending upon which analytical method and which type of component needed to be tested. The calculations required to obtain the active concentrations from the results of these measurements are already programmed into the controller 619 and the control system 222 for various analyzer modules and ECP systems.

By implementing the method 100 of FIG. 1 and the necessary analytical techniques programmed in the controller 619, electrochemical response measurements of the various testing solutions, analytical solutions, etc., as described in FIG. 1 are obtained and the concentration of the component of interest is determined. For example, when analyzing the concentration of copper in a plating bath of unknown components using the method 100 as described herein, a analytical reagent solution made up of 0.4M of magnesium disodium ethelenediaminetetraacetic acid ($MgNa_2EDTA$) and about 100 g/L of glycine is prepared first. Then, a sample of electrolyte from the process cell 240 is flowed into the reaction cell of the chemical analyzer and diluted sufficiently into a testing solution for the chemical analyzer sensor to measure a chemical response, such as electrical potentials and others. Multiple doses of the prepared analytical reagent solution are prepared/titered and mixed with the testing solution (the resulting mixture is sometimes referred to as a production solution) and a series of chemical plating responses is obtained by the automated titration analyzer. Finally, the controller 619 implements a specified analytical technique for copper measurement, such as a titration technique to determine on-line the copper concentration in the plating bath from the process cell 240.

The information from the chemical analyzers 615 and 617 is then communicated to the control system 222. The control system 222 processes the information and transmits signals, which include user-defined chemical dosage parameters, to the dosing controller 611. The received information is used to provide real-time adjustments to the source chemical replenishment rates by operating one or more of the valves 609, thereby maintaining a desired, and preferably constant, chemical composition of the electrolyte throughout the electroplating process. The waste electrolyte from the analyzer module is then flowed to the waste disposal system 622 via the outlet line 621.

The methods described herein provide component analysis of the electrolyte and facilitate a closed-loop analysis that can be performed either manually or with an analyzer attached to the system. The analyzer module 616 shown in FIG. 3 is merely illustrative. In another embodiment, each analyzer may be coupled to the main electrolyte tank by a separate supply line and be operated by separate controllers. Persons skilled in the art will recognize other embodiments.

Various alternatives may be employed for real-time monitoring and adjustments of the plating components. For example, control of the dosing module 603 may be manually adjusted by an operator observing the output values provided by the chemical analyzer module 616. The system software may allow for both an automatic real-time adjustment mode as well as an operator (manual) mode. Further, a single controller or multiple controllers may be used to operate various components of the system such as the chemical analyzer module 616, the dosing module 603, and the heat exchanger 624.

EXAMPLES

Examples of analytical methods for determining the concentration of a component or electrolyte of interest in an acidic or basic metal plating bath are presented herein. The ECP system used herein is an Electra iECP system available from Applied Materials, Inc. of Santa Clara, Calif. along with a G2 titration analyzer. Typical concentrations of the components of a plating bath that may be used in such Electra iECP system are as follows.

The concentrations of the inorganic components may be, for example, between about 5 grams per liter (g/L) to about 80 g/L of copper sulfate, such as between about 10 g/L and about 60 g/L, between about 30 ppm and about 200 ppm of hydrochloric acid, and between about 5 g/L to about 200 g/L of sulfuric acid. The concentrations of the organic components in a plating bath that can be analyzed by the methods described herein may be, for example, between about 0.01 ml/L to about 25 ml/L of an accelerator, brightener, or anti-suppressor, between about 0.01 ml/L and about 60 mL of a suppressor, carrier, surfactant, or wetting agent, and between about 0.01 ml/L to about 20 ml/L of a leveler, over-plate inhibitor, or grain refiner. Various components used herein were purchased from Applied materials, Inc. of Santa Clara, Shipley Inc. of Marborough, Mass., CPI International (CPI) of Santa Rosa, Calif., or Enthone OMI of New Haven, Conn.

Figure 4:
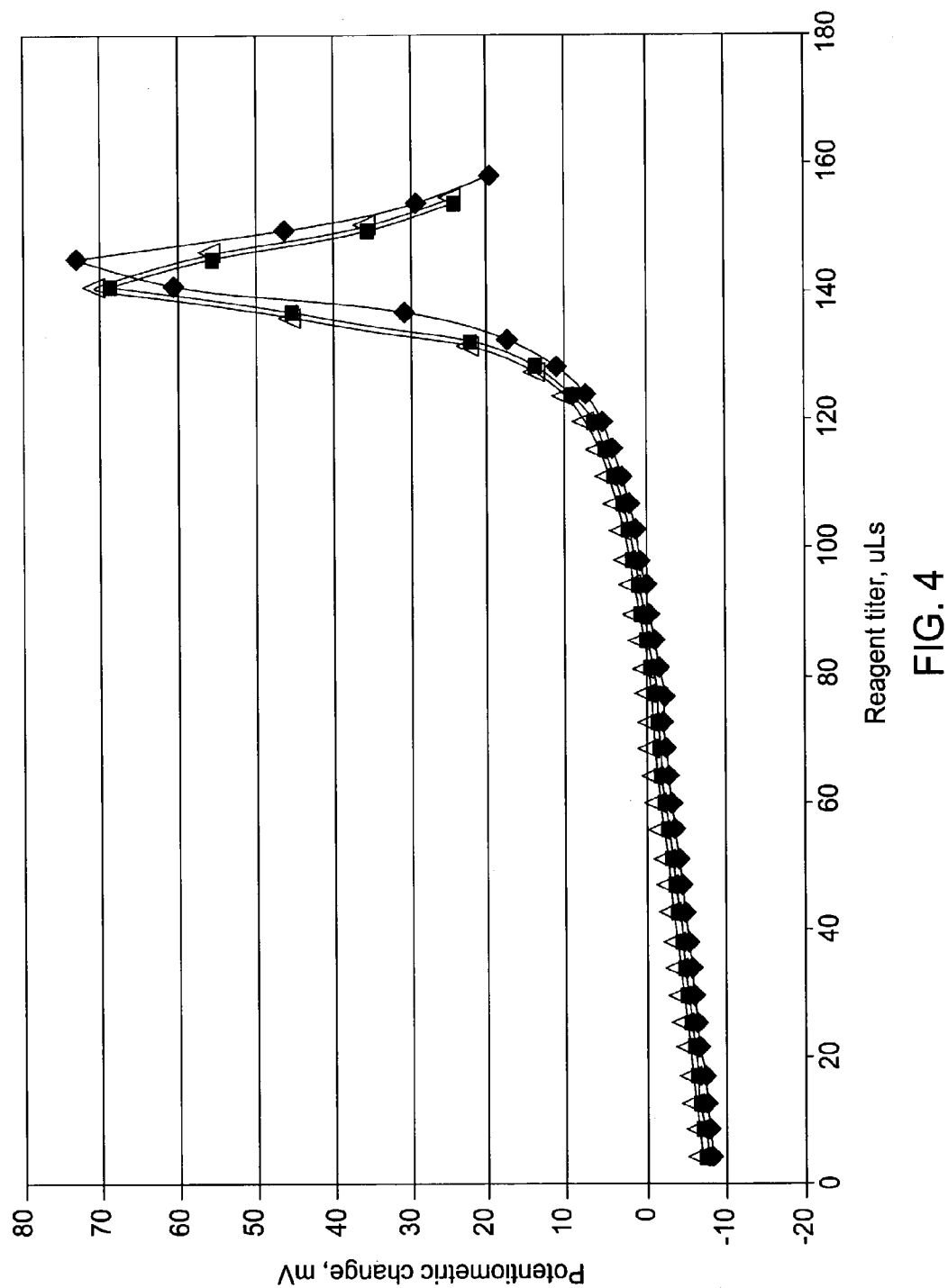
FIG. 4 is a graphical representation of a titration analysis using an analytical reagent solution of the present invention.

FIG. 4 demonstrates three potentiometric titration curves generated while dosing with an analytical reagent solution as described herein to measure copper concentration of a sampled plating bath. In FIG. 4, potentiometric measurements as electrical potentials in units of milivolts at y-axis were plotted against the analytical reagent solution added per titer dose in units of microliters at x-axis. Each titer dose (volume of the analytical reagent solution added) is about 4 microliter. Other volumes of titer dose can also be used.

As shown in FIG. 4, the spike (endpoint) in each of the three titration series/curves is observed, and this endpoint titer dose/volume represents an equilibrium between the total added titer doses of the analytical reagent solution and the sampled plating bath to be measured. The equilibrium is used to calculate the concentration of copper in the sampled plating bath. The analytical reagent solution is compatible with other analyses for measuring the concentrations of other component components for plating, such as the concentration of chloride, and also cleans the analytical equipment from the build-up of deposits and precipitates.

While the foregoing is directed to various embodiments of the invention, other and further embodiments of the invention may be devised without departing from the basic scope thereof. The scope of the invention is determined by the claims that follow.

What is claimed is:

1. An analytical method for determining the concentration of a component in a plating bath, comprising:

providing an analytical reagent solution, wherein the analytical reagent solution comprises at least one chelating agent, at least one pH buffering agent, and water;

providing a testing solution having a portion of the plating bath therein;

measuring a series of chemical responses of the testing solution reacting with two or more doses of the analytical reagent solution; and calculating the concentration of the component in the plating bath from the measurements of the series of chemical responses.

2. The method of claim 1, wherein the method is applied to at least one of titration and back titration.

3. The method of claim 1, wherein the component is copper.

4. The method of claim 1, wherein the at least one chelating agent is selected from the group consisting of ethelenediaminetetraacetic acid ($H_4EDTA$), ethelenediaminetetraacetic acid salts, ethelenediaminetetraacetic acid disodium salt ($Na_2$ $H_2EDTA$), tetrasodium ethelenediaminetetraacetic acid ($Na_4EDTA$), magnesium disodium ethelenediam inetetraacetic acid ($MgNa_2EDTA$), cyclohexanediaminetetraacetic acid (CDTA), N-2-hydroxyethyl-ethylenediamine-N,N,N'-triacetic acid tri sodium salt (HEDTA), triethylene tetramine hexaacetic acid (TTHA), nitrilotriacetic acid (NTA), derivatives, hydrates, anhydrates, metal salts, and combinations thereof.

5. The method of claim 1, wherein the at least one pH buffering agent is selected from the group consisting of ammonia, ammonia chloride, sodium hydroxide, ammonium hydroxide, magnesium hydroxide, and calcium hydroxide, their derivatives, and combinations thereof.

6. The method of claim 1, wherein the at least one pH buffering agent is present in an amount sufficient to adjust the pH of the analytical reagent solution to a range of between about 7 and about 10.

7. The method of claim 1, wherein the at least one pH buffering agent is non-volatile.

8. The method of claim 1, wherein the analytical reagent solution further comprises at least one cleaning agent.

9. The method of claim 8, wherein the at least one cleaning agent is selected from the group consisting of amino acids, amine(—NH2)-containing, thiol(—SH) -containing, thio(—SC)-containing, and thionate (—SO)-containing compounds, their derivatives, and combinations thereof.

10. The method of claim 8, wherein the at least one cleaning agent is selected from the group consisting of glycine, glutamine, and derivatives thereof.

11. The method of claim 8, wherein the at least one cleaning agent is non-volatile.

12. An analytical method for determining the concentration of a component in a plating bath, comprising:

providing an analytical reagent solution, wherein the analytical reagent solution comprises, at least one chelating agent selected from the group consisting of ethelenediaminetetraacetic acid ($H_4EDTA$), ethelenediaminetetraacetic acid salts, ethelenediaminetetraacetic acid disodium salt ($Na_2$ $H_2EDTA$), tetrasodium ethelenediaminetetraacetic acid ($Na_4EDTA$), magnesium disodium ethelenediaminetetraacetic acid ($MgNa_2EDTA$), cyclohexanediaminetetraacetic acid (CDTA), N-2-hydroxyethyl-ethylenediamine-N,N,N'-triacetic acid tri sodium salt (HEDTA), triethylene tetramine hexaacetic acid (TTHA), nitrilotriacetic acid (NTA), derivatives, hydrates, anhydrates, metal salts, and combinations thereof;

at least one pH buffering agent selected from the group consisting of ammonia, ammonia chloride, a hydroxide salt solution, sodium hydroxide, ammonium hydroxide, magnesium hydroxide, and calcium hydroxide, and combinations thereof, in an amount sufficient to adjust the pH of the analytical reagent solution to a range of from about 7 to about 10; and water;

providing a testing solution having a portion of the plating bath therein;

measuring a series of chemical responses of the testing solution reacting with two or more doses of the analytical reagent solution; and calculating the concentration of the component in the plating bath from the measurements of the series of chemical responses.

13. The method of claim 12, wherein the method is applied to an analytical technique selected from the group consisting of titration and back titration.

14. The method of claim 12, wherein the component is copper.

15. The method of claim 12, wherein the at least one analytical reagent solution further comprises at least one cleaning agent selected from the group consisting of amino acids, amine(—NH2)-containing, thiol(—SH)-containing, thio(—SC)-containing, and thionate (—SO)-containing compounds, their derivatives, and combinations thereof.

16. An analytical method for determining the concentration of a component in a plating bath, comprising:

combining two or more reagent solutions for at least one chelating and at least one buffering into one analytical reagent solution, wherein the analytical reagent solution comprises:

at least one chelating agent selected from the group consisting of ethelenediaminetetraacetic acid ($H_4$EDTA), ethelenediaminetetraacetic acid salts, ethelenediaminetetraacetic acid disodium salt ($Na_2H_2$EDTA), tetrasodium ethelenediaminetetraacetic acid ($Na_4$EDTA), magnesium disodium ethelenediaminetetraacetic acid ($MgNa_2$EDTA), cyclohexanediaminetetraacetic acid (CDTA), N-2-hydroxyethyl-ethylenediamine-N,N,N'-triacetic acid tri sodium salt (HEDTA), triethylene tetramine hexaacetic acid (TTHA), nitrilotriacetic acid (NTA), derivatives, hydrates, anhydrates, metal salts, and combinations thereof;

a pH buffering agent selected from the group consisting of ammonia, ammonia chloride, a hydroxide salt solution, sodium hydroxide, ammonium hydroxide, magnesium hydroxide, and calcium hydroxide, and combinations thereof, in an amount sufficient to adjust the pH of the analytical reagent solution to a range of from about 7 to about 10; and water; and performing an analytical technique for a portion of the plating bath using the analytical reagent solution to determine the concentration of the component.

17. The method of claim 16, wherein the analytical technique is selected from the group consisting of titration and back titration.

18. The method of claim 16, wherein the component is copper.

19. The method of claim 16, wherein the analytical reagent solution further comprises at least one cleaning agent selected from the group consisting of amino acids, amine(—NH2)-containing, thiol(—SH)-containing, thio(—SC)-containing, and thionate (—SO)-containing compounds, their derivatives, and combinations thereof.

20. An analytical method for determining the concentration of a component in a plating bath, comprising:

providing a testing solution having a portion of the plating bath therein;

adding a pre-dose volume of an analytical reagent solution to react with the testing solution;

adding one or more doses of a second volume of the analytical reagent solution to react with the testing solution;

measuring a series of chemical responses of the testing solution reacting with the analytical reagent solution;

obtaining an endpoint dose; and calculating the concentration of the component in the plating bath from the measurements of the series of chemical responses and the endpoint dose, wherein the analytical reagent solution comprises:

at least one chelating agent selected from the group consisting of ethelenediaminetetraacetic acid ($H_4$EDTA), ethelenediaminetetraacetic acid salts, ethelenediaminetetraacetic acid disodium salt ($Na_2H_2$EDTA), tetrasodium ethelenediaminetetraacetic acid ($Na_4$EDTA), magnesium disodium ethelenediaminetetraacetic acid ($MgNa_2$EDTA), cyclohexanediaminetetraacetic acid (CDTA), N-2-hydroxyethyl-ethylenediam me-N,N,N'-triacetic acid tri sodium salt (HEDTA), triethylene tetramine hexaacetic acid (TTHA), nitrilotriacetic acid (NTA), derivatives, hydrates, anhydrates, metal salts, and combinations thereof;

at least one pH buffering agent selected from the group consisting of ammonia, ammonia chloride, a hydroxide salt solution, sodium hydroxide, ammonium hydroxide, magnesium hydroxide, and calcium hydroxide, and combinations thereof, in an amount sufficient to adjust the pH of the analytical reagent solution to a range of from about 7 to about 10; and water.

21. The method of claim 20, wherein the pre-dose volume is larger then the second volume.

22. The method of claim 20, wherein the pre-dose volume is about 10 times to about 100 times the second volume.

23. The method of claim 20, wherein the method is applied to an analytical technique selected from the group consisting of titration and back titration.

24. The method of claim 20, wherein the component is copper.

25. The method of claim 20, wherein the analytical reagent solution further comprises at least one cleaning agent selected from the group consisting of amino acids, amine(—NH2)-containing, thiol(—SH)-containing, thio(—SC)-containing, and thionate (—SO)-containing compounds, and their derivatives and combinations thereof.

* * * * *

UNITED STATES PATENT AND TRADEMARK OFFICE
CERTIFICATE OF CORRECTION

| | |
|---|---|
| PATENT NO. | : 7,205,153 B2 |
| APPLICATION NO. | : 10/412484 |
| DATED | : April 17, 2007 |
| INVENTOR(S) | : Balisky |

It is certified that error appears in the above-identified patent and that said Letters Patent is hereby corrected as shown below:

Title page, item [57]
Line 9, please delete "regent" and insert --reagent-- therefor;

Column 2, Line 36, please delete "a" and insert --an-- therefor;

Column 5, Line 21, please delete "bases" and insert --basis-- therefor;

Column 6, Line 36, please delete "an" and insert --a-- therefor;

Column 7, Line 35, please delete "an" and insert --a-- therefor;

Column 8, Line 4, please delete "is" and insert --are-- therefor;

Column 12, Line 31, please delete "a" and insert --an-- therefor;

Column 13, Line 32, please delete "60 mL" and insert --60 ml/L-- therefor;

Column 13, Line 44, please delete "milivolts" and insert --millivolts-- therefor;

Column 13, Line 56, please delete "component";

Column 14, Claim 4, Lines 21-22, please delete "ethelenediam inetetraacetic"and insert --ethelenediaminetetraacetic-- therefor;

Column 14, Claim 4, Line 23, please delete "ethelenediam inetetraacetic" and insert --ethelenediaminetetraacetic-- therefor;

Column 16, Claim 20, Line 33, please delete "N-2-hydroxyethyl-ethylenediam me-N" and insert --N-2-hydroxyethyl-ethylenediamine-N-- therefor;

Signed and Sealed this
Twenty-seventh Day of September, 2011

David J. Kappos
*Director of the United States Patent and Trademark Office*

CERTIFICATE OF CORRECTION (continued)
U.S. Pat. No. 7,205,153 B2

Column 16, Claim 21, Line 47, please delete "then" and insert --than-- therefor.